US00PP09795P

United States Patent [19]

Schumann et al.

[11] Patent Number: Plant 9,795

[45] Date of Patent: Feb. 4, 1997

[54] GERANIUM PLANT NAMED 'FISLAIS'

[75] Inventors: Ingeborg Schumann, Albstadt; Angelika Utecht, Montabaur, both of Germany

[73] Assignee: Florfis AG, Binningen, Switzerland

[21] Appl. No.: 532,503

[22] Filed: Sep. 22, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fislais, characterized by its salmon-pink and white semi-double flowers, medium green foliage with very strong zonation, relatively compact, bushy growth habit and good branching ability.

1 Drawing Sheet

The present invention comprises a new and distinct cultivar of geranium, botanically known as *Pelargonium zonale*, and hereinafter referred to by the cultivar name Fislais.

Fislais is a product of a planned breeding program which had the objective of creating new geranium cultivars with salmon flower color, medium green foliage and zonation.

Fislais was originated from a hybridization made by inventor Ingeborg Schumann in a controlled breeding program in Galdar, Gran Canaria, Spain in 1987. The female parent was an unnamed hybrid seedling identified as K86/122/2 and characterized by single salmon colored flowers and compact plant habit. It was obtained by a series of crossings between the commercial varieties Hoennefruehling, Bianca, Achspen and Wienerblut. Hoennefruehling has single light pink flowers and starts flowering very early. Bianca is characterized by white single flowers, late flower response and tall plant habit. Achspen, disclosed in U.S. Plant Pat. No. 5,313 is characterized by salmon rose semi-double flowers in combination with compact plant habit and foliage without zonation. Wienerblut, disclosed in U.S. Plant Pat. No. 5,931 under the varietal name Waltz, has single orange flowers, large umbels on strong peduncles and dark green foliage with strong zonation.

The male parent of Fislais was the commercial variety Palais, disclosed in U.S. Plant Pat. No. 5,315, and characterized by salmon pink semi-double flowers, foliage with strong zonation, and medium to vigorous growth.

Fislais was discovered and selected as one flowering plant within the progeny of the stated cross by Ingeborg Schumann in 1988 in a controlled environment in Galdar, Gran Canaria, Spain.

The first act of asexual reproduction of Fislais was accomplished when vegetative cuttings were taken from the initial selection in autumn 1990 in a controlled environment in Galdar, Gran Canaria, Spain, by, or under the supervision of, inventory Angelika Utecht.

Horticultural examination of plants grown from these cuttings initiated in May 1991 in Hillscheid, Federal Republic of Germany, and continuing thereafter, has demonstrated that the combination of characteristics as herein disclosed for Fislais are firmly fixed and are retained through successive generations of asexual reproduction.

Fislais has not been observed under all possible environmental conditions. The phenotype may vary significantly with variations in environment such as temperature, light intensity and daylength, without, however, any variance in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fislais, which in combination, distinguish this geranium as a new and distinct cultivar:

1. Salmon-pink and white flower color.
2. Semi-double medium sized florets.
3. Medium green foliage with very strong zonation.
4. Medium early flowering.
5. Comparatively compact plant habit.
6. Good branching ability.

Of the many commercial cultivars known to the present inventor, the most similar in comparison to Fislais are the parent variety Palais, and the cultivar Fislesse, disclosed in a copending application. In comparison to Palais, Fislais has a more compact bushy plant habit, and its peduncles are a little shorter but stronger thereby providing rigid support for the flowers. In comparison to Fislesse, Fislais has less uniform flower color, with the center of the flower being more intense salmon colored while the tips of petals near the margin are white. Furthermore, foliage of Fislais is strongly zoned, while Fislesee has no or only very weak zonation.

The accompanying photographic drawing shows typical flower and foliage characteristics of Fislais, with colors being as true as possible with illustrations of this type.

In the following description, color references are made to The Royal Horticultural Society (R.H.S.) Colour Chart. The color values were determined indoors from flowers taken from plants grown in a greenhouse in May 1994 in Hillscheid, Federal Republic of Germany.

Classification:

*Botanical.*—A hybrid of the species *Pelargonium zonale l'Hert.*

*Commercial.*—Zonal geranium, cv. Fislais.

Inflorescence

Umbel:

*Shape.*—Semi-spherical.

*Average diameter.*—80 mm.

*Average depth.*—45 mm.

*Peduncle length.*—110 mm.

*Peduncle color.*—Green, slightly reddish.

*Pedicel length.*—18 mm.

*Pedicel color.*—Slightly reddish.

*Number of open flowers per umbel.*—25.

Corolla:

*Average diameter.*—40 mm.

*Form.*—Semi-double.

*Number of petals.*—8–9.

*Number of petaloids.*—2–3.
*Color (general tonality from a distance of three meters).*—Salmon pink and white.
*Color of upper surface of petal near center.*—43 B-C.
*Color of petal near margin.*—56 C.
*Color of lower surface of petals.*—52 D or lighter.
*Color of sepals.*—Light green.
*Number of sepals.*—5.

Bud:
*Shape.*—Elliptical.
*Color (adaxial).*—Light green.
*Color (abaxial).*—White and salmon pink, marbled.

Reproductive organs:
*Androecium.*—4–5 fertile anthers, filaments white and salmon, orange pollen.
*Gynoecium.*—5–6 lobed stigma, salmon style and at stigma.
*Seed.*—No seed set observed.

Spring flowering response period.In Hillscheid, Germany, in 1994 plants had on average 0.8 umbels with at least one flower opened 11 weeks after planting of unrooted cuttings.

Outdoor flower production: The flower count in 1994 in Hillscheid, Germany, indicated about 30 umbels per plant for May through August observation period.

Durability: Good shatter resistance and rain resistance.

Plant

Foliage:
*Form.*—Kidney-shaped.
*Margin.*—Bicrenated.
*Size of leaf.*—85 mm.
*Color of upper surface.*—Medium green, approximately 137 B.
*Color of zonation.*—Dark brown, 200 B.
*Tolerance of botrytis.*—Average.

General appearance and form:
*Internode length.*—5 mm.
*Branching pattern.*—1.7 branches per week.
*Length of plants.*—26 cm (in June, 16-week-old plants).

Ploidy: Tetraploid.

It is claimed:

1. A new and distinct cultivar of geranium plant named Fislais, as illustrated and described.

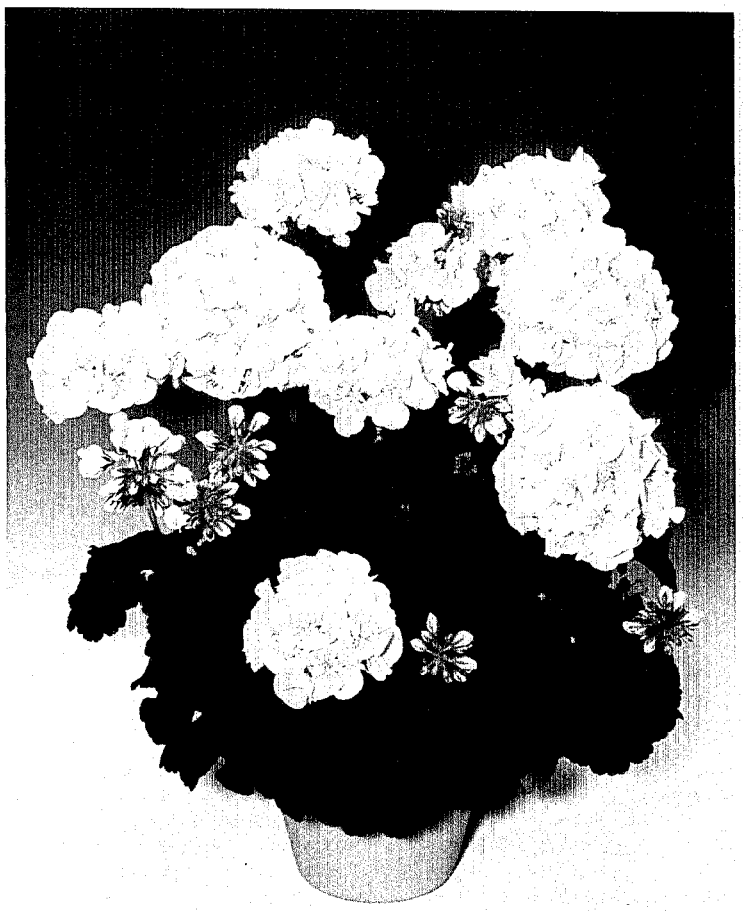

* * * * *